United States Patent [19]

Ollivier

[11] Patent Number: 5,719,316
[45] Date of Patent: Feb. 17, 1998

[54] PROCESS FOR THE PREPARATION OF LAURYLLACTAM BY PHOTONITROSATION OF CYCLODODECANE IN THE PRESENCE OF TRICHLORONITROSOMETHANE

[75] Inventor: Jean Ollivier, Arudy, France

[73] Assignee: Elf Atochem S.A., France

[21] Appl. No.: 822,488

[22] Filed: Mar. 24, 1997

[30] Foreign Application Priority Data

Mar. 25, 1996 [FR] France ................................ 96 03687

[51] Int. Cl.$^6$ ................................................. C07C 249/06
[52] U.S. Cl. ....................................... 564/253; 204/157.83
[58] Field of Search ................ 564/253; 204/157.83

[56] References Cited

FOREIGN PATENT DOCUMENTS

| 2094612 | 2/1972 | France . |
|---|---|---|
| 2001331 | 7/1970 | Germany . |
| 1136747 | 12/1968 | United Kingdom . |

OTHER PUBLICATIONS

French Search Report dated Dec. 20, 1996.

Chemical Abstracts–vol.76, 1972–p.424, No. 126097z.

Tetrahedron Letters No. 7, 1972–pp. 593–596, B. G. Gowenlock et al.

*Primary Examiner*—Richard L. Raymond
*Attorney, Agent, or Firm*—Bell, Boyd & Lloyd

[57] ABSTRACT

The subject-matter of the invention is a process for the preparation of cyclododecanone oxime by photonitrosation of cyclododecane in the presence of hydrochloric acid, characterized in that the nitrosing agent is trichloronitrosomethane.

8 Claims, No Drawings

PROCESS FOR THE PREPARATION OF LAURYLLACTAM BY PHOTONITROSATION OF CYCLODODECANE IN THE PRESENCE OF TRICHLORONITROSOMETHANE

FIELD OF THE INVENTION

The present invention relates to the field of polymers of the polyamide 12 type which are obtained by polymerization of lauryllactam. It relates more particularly to a process for the preparation of cyclododecanone oxime (reaction intermediate of lauryllactam) by photonitrosation of cyclododecane in the presence of trichloronitrosomethane.

BACKGROUND OF THE INVENTION

Lauryllactam is widely employed as monomer for the preparation of polyamide 12 by polymerization. Many methods for its preparation are described in the literature (see, for example, "Procédés de Pétrochimie" ["Processes of Petrochemistry"], volume 2, pp. 316–322, published by Technip, 1986).

The most widely known industrial processes are those which have been developed by Hüls and Ato Chimie from cyclododecane, Snia Viscosa from cyclododecatriene monoozonide and UBE from cyclododecanone.

More precisely, lauryllactam is obtained according to the process proposed by Ato Chimie in two stages:

in the first stage cyclododecanone oxime is formed by photonitrosation of cyclododecane according to the following reaction:

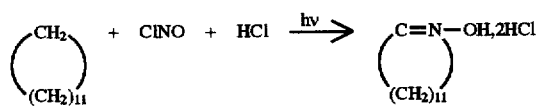

and, in the second stage, the oxime thus formed is subjected to a Beckmann rearrangement in the presence of sulphuric acid

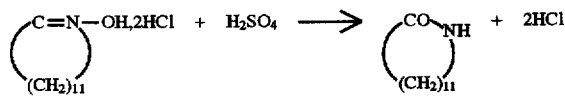

In the first stage the photonitrosation is carried out in the presence of nitrosyl chloride, which compound also turns out to be an agent which chlorinates cyclododecane. Chlorine-containing by-products are thus formed, such as chloroalkanes and chlorooximes. Such compounds, which cannot be profitably exploited, are detrimental both to the yield and to the selectivity of the reaction, and to the quality of the final product, and must therefore be removed by means of lengthy and costly purifications.

It has now been found that the use of trichloronitrosomethane as nitrosing agent enables the selectivity to be improved by preventing the formation of the abovementioned chlorine-containing by-products, while retaining the advantages linked with the photonitrosation.

DESCRIPTION OF THE INVENTION

The subject-matter of the invention is therefore a new process for the preparation of cyclododecanone oxime by photonitrosation of cyclododecane in the presence of hydrochloric acid, characterized in that the nitrosing agent is trichloronitrosomethane.

The trichloronitrosomethane of the process according to the invention is generally formed from nitrosyl chloride and chloroform by a conventional photochemical reaction, for example in a reactor comprising mercury or sodium vapour lamps. The photochemical reaction is generally performed at a temperature of between 10° and 20° C., at atmospheric pressure. The weight concentration of nitrosyl chloride in chloroform is preferably between 2 and 10 g/l.

The trichloronitrosomethane is employed in the form of a solution in chlorinated solvents, preferably chloroform.

The weight concentration of trichloronitrosomethane in the abovementioned solvent is generally between 0.2 and 20 g/l and preferably between 8 and 12 g/l.

The hydrochloric acid is generally used in the form of gaseous and anhydrous hydrochloric acid.

The cyclododecane may be obtained by methods which are known to a person skilled in the art, for example by cyclotrimerization of butadiene and hydrogenation of the cyclododecatriene formed.

The process according to the invention is performed by direct conversion of the mixture consisting of cyclododecane, hydrochloric acid and trichloronitrosomethane in conventional photochemical conditions.

In order to facilitate the extraction of the oxime during the subsequent stage of phase separation, a small quantity of sulphuric acid whose assay is between 75 and 98% by weight is advantageously added to the mixture.

The mixture is generally irradiated at a temperature of between 0° and 30° C. by means of mercury or sodium vapour lamp(s) emitting between 400 and 600 nm and preferably 500 and 600 nm.

The process according to the invention is generally carried out at atmospheric pressure.

At the end of the reaction the mixture is subjected to a phase separation and the cyclododecanone oxime is recovered in the aqueous phase.

The oxime thus formed can be employed for the preparation of lauryllactam, for example by Beckmann rearrangement in the presence of sulphuric acid.

EXAMPLES

The following examples illustrate the invention without, however, limiting it.

EXAMPLE

A photochemical reactor is employed which is equipped with a central immersion lamp-carrier and a 250 watt intermediate pressure sodium vapour lamp emitting a radiation maximum in the vicinity of 595 nm. The lamp-carrier and the lamp are thermostated by circulating water at 15° C.

Thus equipped, the reactor has a working volume of 250 ml and the lamp has an optical path of 6.5 mm.

The introduction of the reactants is carried out at atmospheric pressure by means of a tube equipped with a sinter (porosity 4) situated in the lower part of the reactor.

The gaseous effluents originating from the reactor are, after circulation in a cooled device (temperature 0° C.), directed towards a bubbler containing a sodium hydroxide solution and connected to a flare.

a) Preparation of trichloronitrosomethane

Into the reactor are introduced 200 ml of chloroform in which nitrosyl chloride is gradually dissolved until the concentration is 2 g/l. The lamp is switched on and irradiation is carried out for 3 hours while a uniform flow rate of 2 l/h of nitrosyl chloride is maintained.

After switching off the lamp and stopping the injection of nitrosyl chloride the mixture obtained is placed in a stream of nitrogen in order to remove unreacted nitrosyl chloride. The appearance of a blue colour characteristic of trichloronitrosomethane (presence of a band at 592 nm; $\epsilon$: 5.57 mol$^{-1}$ l cm$^{-1}$) is then noted.

The concentration of trichloronitrosomethane in chloroform is 10 g/l.

b) Photonitrosation of cyclododecane

The abovementioned chloroform solution of trichloronitrosomethane, to which are added 25 ml of 85% sulphuric acid, 2 g of gaseous hydrochloric acid and 17 g of cyclododecane, is irradiated for 90 minutes with stirring by means of a pump (renewal of the reactor volume: 100 times per hour).

At the end of the reaction the mixture obtained, which has lost its blue colour, is separated.

The aqueous phase recovered contains 2.59 g of cyclododecanone oxime (i.e. a 97.7% yield, calculated on the basis of the trichloronitrosomethane introduced) and no chlorooxime.

The residual organic phase contains no chlorine-containing derivative of the starting cyclododecane.

COMPARATIVE EXAMPLE

The operation is carried out in the reactor described in the preceding example, the nitrosing agent employed being nitrosyl chloride.

Gaseous nitrosyl chloride is injected continuously into the reactor containing 200 ml of a solution of cyclododecane in chloroform (300 g/l) and 20 ml of sulphuric acid at a concentration of 85% by weight, in such a way that after the lamp is switched on, the concentration in the reaction mixture is 2 g/l.

The reaction mixture, stirred by means of an external pump (renewal of the reactor volume: 100 times per hour) is irradiated for 2 hours.

At the end of the reaction the reaction mixture is separated.

Cyclododecanone oxime (molar selectivity: 8.35%) and chlorooximes (5.4% by weight of the mixture) are recovered in the aqueous phase.

The organic phase contains, besides the residual cyclododecane, mono- and dichloro derivatives of cyclododecane, 4.95 and 1.65% by weight, respectively, of the starting cyclododecane.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. Process for the preparation of cyclododecanone oxime comprising photonitrosation of cyclododecane in the presence of hydrochloric acid and of a nitrosing agent, characterized in that the nitrosing agent is trichloronitrosomethane.

2. Process according to claim 1, wherein the trichloronitrosomethane is in solution in chloroform.

3. Process according to claim 2, wherein the weight concentration of tricloronitrosomethane is between 0.2 and 20 g/l.

4. Process according to claim 1, wherein the wavelength of the luminous radiations is between 400 and 600 nm.

5. Process according to claim 1, wherein the temperature of photonitrosation is between 0° and 30° C.

6. Process according to claim 1, wherein the operation is carried out at atmospheric pressure.

7. Process according to claim 1, wherein the trichloronitrosomethane is prepared by photonitrosation from nitrosyl chloride and chloroform.

8. Process for the preparation of lauryllactam comprising preparing the cylclododecanone oxime by photonitrosation of cyclododecane in the presence of hydrochloric acid and trichloronitrosomethane, and submitting the oxime thus formed to a Beckmann rearrangement.

* * * * *

UNITED STATES PATENT AND TRADEMARK OFFICE
CERTIFICATE OF CORRECTION

PATENT NO.   : 5,719,316
DATED        : February 17, 1998
INVENTOR(S)  : Jean OLLIVIER It is certified that error appears in the above-indentified patent and that said Letters Patent is hereby corrected as shown below:

Claim 3, line 2, change "tricloronitrosomethane" to read
  --trichloronitrosomethane--;

Claim 8, line 2, change "cylclododecanone" to read
  --cyclododecanone--.

Signed and Sealed this

Twenty-third Day of June, 1998

Attest:

BRUCE LEHMAN

*Attesting Officer*    *Commissioner of Patents and Trademarks*